United States Patent [19]

Chinn et al.

[11] Patent Number: 4,801,611

[45] Date of Patent: Jan. 31, 1989

[54] 5-LIPOXYGENASE INHIBITORS

[75] Inventors: Leland J. Chinn, Montebello, Calif.; Bipinchandra N. Desai, Vernon Hills; Richard A. Mueller, Glencoe, both of Ill.

[73] Assignee: G. D. Searle & Co., Chicago, Ill.

[21] Appl. No.: 47,237

[22] Filed: May 7, 1987

[51] Int. Cl.$^4$ .................. A61U 31/19; A61U 31/235
[52] U.S. Cl. ................................. 514/532; 514/570
[58] Field of Search ............................. 514/570, 532

[56] References Cited

U.S. PATENT DOCUMENTS

| | | | |
|---|---|---|---|
| 4,012,523 | 3/1977 | Wagner | 514/570 |
| 4,067,998 | 1/1978 | Wagner | 514/570 |
| 4,108,831 | 8/1978 | Cottman | 260/609 D |
| 4,198,425 | 4/1980 | Mitsui et al. | 260/343.5 |
| 4,262,013 | 4/1981 | Mitsui et al. | 260/343.5 |

FOREIGN PATENT DOCUMENTS 867421 11/1978 Belgium .

OTHER PUBLICATIONS

Foegh et al. Improved Rat Cardiac Allograft Survival with Non-Steroidal Pharm Agents., Transplant Proc., 19,1297–1300 (Feb. 1987).
Foegh et al., Presentation at 6th Int Conf. On Prostaglandins and Related cpds., Florence, Italy, Jun. 3–6, 1987 (abstract attached).
Foegh, et al., Presentation at NIH Workshop, Potential Therapeutic use of Inhibitors of Leukotriene . . . , Jun. 23, 1986 (trip report attached).
Wagner, E. R. et al., "Hypolipidemic Arylthioalkanoic Acids", J. Med. Chem., 1977, vol. 20, No. 8, 1007–1013.

Primary Examiner—Stanley J. Friedman
Attorney, Agent, or Firm—Mary Jo Kanady; Paul D. Matukaitis

[57] ABSTRACT

This invention encompasses compounds and methods for inhibiting lipoxygenase and includes a pharmaceutical composition comprising a pharmaceutical carrier and an effective lipoxygenase inhibiting amount of a compound of the formula:

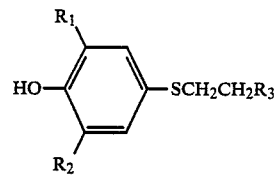

wherein $R_1$ and $R_2$ are the same or different members of the group consisting of tert-alkyl of 4 to 10 carbon atoms; and $R_3$ is

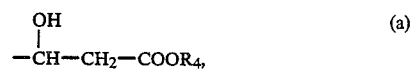

(a)

wherein $R_4$ is hydrogen or lower alkyl;

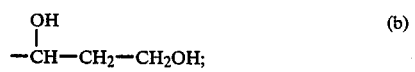

(b)

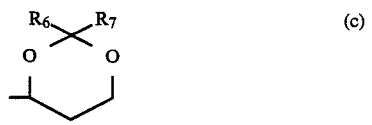

(c)

wherein $R_6$ and $R_7$ may be the same or different and are alkyl of 1 to 4 carbon atoms; or

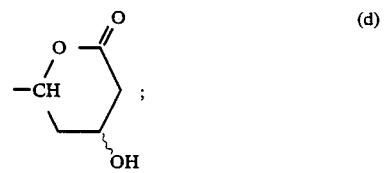

(d)

and the pharmaceuticlaly acceptable salts thereof.

The compounds and pharmaceutical formulations of the present invention are 5-lipoxygenase inhibitors and, therefore, are useful in the treatment of local and systemic inflammation, allergy and hypersensitivity reactions and other disorders in which agents formed in the 5-lipoxygenase metabolic pathway are involved.

8 Claims, No Drawings

5-LIPOXYGENASE INHIBITORS

BACKGROUND OF THE INVENTION

A. Field of the Invention

The present invention relates to compounds and pharmaceutical compositions which inhibit lipoxygenase and are useful as anti-inflammatory and anti-allergy agents.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs, TRIHETEs) and hydroperoxyeicosatetraenoic acids (HPETEs) and the leukotrienes, all of which have potent physiological effects. The leukotrienes, which are produced via the 5-lipoxygenase pathway, are the major contributors to the onset of the symptoms of asthma, and are mediators for immediate hypersensitivity reactions and inflammation.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other immediate hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. The infiltration of eosinophils is one of the histologic features of a variety of allergic reactions. $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flare in the joint which is associated with elevated levels of $LTB_4$. $LTB_4$ is also present in gouty effusions; and exposure to urate crystals is known to stimulate $LTB_4$ production by neutrophils. Accordingly, the 5-lipoxygenase inhibitors of the present invention through inhibition of neutrophil attraction and activation in arthritic joints should reduce the protease and oxidative burden believed responsible for joint destruction in arthritic diseases.

With the exception of benoxaprofen which has 5-lipoxygenase activity, aspirin and the other non-steroidal anti-inflammatory agents (NSAIDs) such as indomethacin, ibuprofen, fenoprofen, and the like, inhibit the synthesis of prostaglandins via the cyclooxygenase pathway of arachidonic acid metabolism. These prostaglandin synthetase inhibitors generally exhibit anti-inflammatory, anti-pyretic and analgesic activity, and are widely used in the treatment of arthritis. The non-steroidal anti-inflammatory agents can lead to the formation of additional pro-inflammatory derivatives of arachidonic acid produced through the 5-lipoxygenase pathway which play a role in immediate hypersensitivity reactions and also have pronounced inflammatory effects. Administration of the NSAIDs alone can produce allergic reactions including bronchospastic reactivity, skin rashes, syndrome of abdominal pain, fever, chills, nausea and vomiting, and anaphylaxis. For this reason, aspirin and the other non-steroidal anti-inflammatory agents (NSAIDs) are generally contraindicated for patients suffering from asthma or who have previously exhibited allergic sensitivity to aspirin or other NSAIDs. Co-administration of the 5-lipoxygenase inhibitors of this invention with cyclooxygenase inhibitors may mitigate the untoward side effects of the latter and allow the increased advantageous use of such cyclooxygenase inhibitors.

Prior to the recognition of the significance of the 5-lipoxygenase pathway of arachidonic acid metabolism in allergic reactions and inflammation, the search for effective therapeutic agents was based primarily on those agents which treated the symptoms of allergy and inflammation. There has since been an effort to develop new drugs which selectively block the formation of the mediators of these conditions, and the present invention provides hydroxyalkylthiophenols which are inhibitors of the 5-lipoxygenase pathway and are useful in the treatment of asthma, rheumatoid arthritis, psoriasis, and other allergy, hypersensitivity reactions, and inflammatory conditions.

To date, benoxaprofen has been the only commercial anti-inflammatory agent which has 5-lipoxygenase inhibition activity. Prior to its withdrawal from the market because of untoward side effects, benoxaprofen was considered to represent a significant advance in the treatment of crippling arthritis and psoriasis. Thus, there remains a longstanding need for agents which block the mechanisms responsible for inflammation and allergic reactions, and which can be safely employed to treat, for example, arthritis, asthma, psoriasis and other dermatoses, allergic reactions and other 5-lipoxygenase mediated conditions. A need also exists for agents which can be administered with the inhibitors of other lipoxygenase enzymes, e.g. cyclo-oxygenase, to mitigate their side effects and support their desirable medicinal properties.

See Bengt Samuesson, "Leukotrienes: Mediators of Immediate Hypersensitivity Reactions and Inflammation", *Science*, Vol. 220, pp. 568–575 (May 1983); Michael K. Bach, "Inhibitors of Leukotriene Synthesis and Action", *The Leukotrienes, Chemistry and Biology*, pp 163–194 (Academic Press, Inc., 1984); C. W. Lee et al., "Human Biology and Immunoreactivity of Leukotrienes", *Advances in Inflammation Research*, Volume 6, pp 219–225 (Raven Press, New York 1984); Editorial, "Leukotrienes and other Lipoxygenase Products in the Pathogenesis and Therapy of Psoriasis and Dermatoses", *Arch. Dermatol*, Vol. 119, pp 541–547 (July, 1983); Robert A. Lewis et al., "A Review of Recent Contributions on Biologically Active Products of Arachidonate Conversion", *Int. J. Immunopharmac.*, Vol. 4, No. 2, pp 85–90 (1982); Michael K. Bach, *Biochemical Pharmacology*, Vol. 23, No. 4, pp 515–521 (1984); and E. L. Becker, *Chemotactic Factors of Inflammation*, pp 223–225 (Elsevier Science Publishers V.B., Amsterdam, 1983); Sharon, P. and Stenson, W. F., *Gastroenterology*, Vol. 84, 454 (1984); and Musch, M. W. et al., *Science*, Vol. 217, 1255 (1982).

The present invention provides compounds which block the 5-lipoxygenase metabolic pathway and, therefore, block the formation of the leukotrienes responsible for allergy and inflammation, and represent a new class of therapeutic agents which are useful in the treatment of allergic and hypersensitivity reactions and inflammation, alone, or also may be utilized in combination with cyclooxygenase inhibitors such as the non-steroidal anti-inflammatory agents.

B. Prior Art

Wagner et al. U.S. Pat. No. 4,029,812, and related U.S. Pat. Nos. 4,076,841 and 4,078,084 which issued from divisional applications of the -812 application, all assigned to the Dow Chemical Company, disclose 2-(3,5-di-tert-butyl-4-hydroxyphenyl)thiocarboxylic acids, esters and simple amides which are hypolipidemics and are useful in reducing plasma lipid levels, especially cholesterol and triglyceride levels.

The Wagner et al. and related compounds have also been reported in the literature as plasticizers and pesticides. See for example, Khim. Tekhnol. 20(4), 568–574 (1977); German Offenlegenschrift DE 2716125 (1977); Pestic. Biochem. Physiol. 1979, 12(1), 23–30.

Primary sulfide alcohols having hindered phenol groups have been reported in the literature as plasticizers, stabilizers, anti-oxidants and elastomers. See U.S. Pat. No. 4,108,831 which discloses hydroxyalkylthiophenols used as antioxidants to stabilize polymers against oxidative degradation; CA81(21:135705b; CA82(18):112655s; CA82(13):86191r; CA82(13):86190q; Eur. Pat. Appl. EP 60799 Al; and CA82(13):86196w.

Cottman, U.S. Pat. No. 4,108,831 discloses antioxidants for the stabilization of polymers and other materials subject to oxidative degradation which have the formula

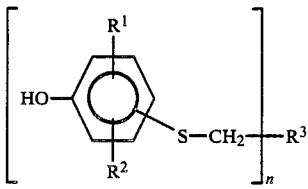

wherein $R^1$ and $R^2$ are selected from the group consisting of hydrogen and hydrocarbon radicals containing 1 to 12 carbon atoms, $R^3$ is a monohydroxy or dihydroxy substituted radical containing 1 to 11 carbon atoms, at least one carbon atom of which is non-aromatic, more particularly a part of a non-cyclic (open chain) aliphatic radical. The non-aromatic portion of $R^3$ contains the hydroxy substitution with the proviso that when $R^3$ contains 2 hydroxy substituents the substituents are located on different carbon atoms, wherein n is 1 or 2 and wherein the thio radical is attached to the phenolic ring in a position ortho or para to the hydroxy group, with the further proviso that when n is 1, $R^3$ is a saturated or unsaturated hydrocarbon radical and when n is 2, $R^3$ is a saturated hydrocarbon radical which can contain 1 or 2 oxyether linkages, i.e. —O—.

A preferred embodiment includes those compounds wherein $R^1$ and $R^2$ are hydrogen or tertiary alkyl radicals having 4 to 9 carbon atoms and are located in the positions ortho to the hydroxy group, and wherein the thio group or groups are in positions para to the hydroxy groups, and wherein n is 1 and $R^3$ has the structural formula

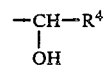

wherein $R^4$ is selected from the group consisting of hydrogen, methyl or phenyl and wherein n is 2 and $R^3$ is the group

SUMMARY OF THE INVENTION

This invention encompasses compounds and methods for inhibiting lipoxygenase and includes pharmaceutical formulations comprising a pharmaceutical carrier and an effective lipoxygenase inhibiting amount of a compound of the formula

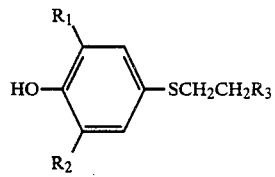

wherein $R_1$ and $R_2$ are the same or different members of the group consisting of tert-alkyl of 4 to 10 carbon atoms; and $R_3$ is

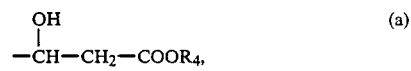

wherein $R_4$ is hydrogen or lower alkyl;

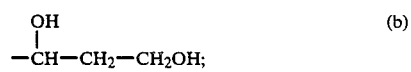

wherein $R_6$ and $R_7$ may be the same or different and are alkyl of 1 to 4 carbon atoms; or

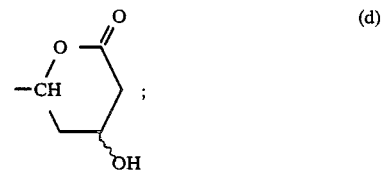

and the pharmaceutically acceptable salts thereof.

It is an object of the present invention to provide methods for promoting anti-allergic and anti-inflammatory effects in mammals in need thereof by the administration of preselected dosages of the compounds of the present invention or pharmaceutically acceptable salts thereof in appropriate non-toxic pharmaceutical dosage forms or compositions.

Another object of the present invention is to provide dosage unit forms adapted for, e.g., oral and/or parenteral administration and useful in the treatment, management and mitigation of allergies, inflammation and hypersensitivity reactions and related disorders and conditions in which physiologically active agents formed in the 5-lipoxygenase metabolic pathway are involved.

DETAILED DESCRIPTION OF THE PREFERRED EMBODIMENTS

These and other similar objects, advantages and features are accomplished according to the products, compositions and methods of the invention comprised of compounds of the formula $$\underset{R_2}{\overset{R_1}{\text{HO}-\text{C}_6\text{H}_2-\text{SCH}_2\text{CH}_2\text{R}_3}}$$

wherein $R_1$ and $R_2$ are the same or different members of the group consisting of tert-alkyl of 4 to 10 carbon atoms; and $R_3$ is (a) $-\overset{OH}{\underset{|}{CH}}-CH_2-COOR_4,$ wherein $R_4$ is hydrogen or lower alkyl;

(b) $-\overset{OH}{\underset{|}{CH}}-CH_2-CH_2OH;$ (c) $\underset{O\quad O}{\overset{R_6\quad R_7}{\times}}$ wherein $R_6$ and $R_7$ may be the same or different and are alkyl of 1 to 4 carbon atoms; or (d) $-CH\underset{OH}{\overset{O}{\diagup}}\overset{O}{\diagdown};$ and the pharmaceutically acceptable salts thereof.

Preferred compounds of the present invention are those compounds of the formula $$\underset{C(CH_3)_3}{\overset{C(CH_3)_3}{\text{HO}-\text{C}_6\text{H}_2-\text{S}-\text{CH}_2\text{CH}_2\text{R}_3}}$$

wherein $R_3$ is (a) $-\overset{OH}{\underset{|}{CH}}-CH_2-COOR_4;$ wherein $R_4$ is hydrogen or methyl (b) $-\overset{OH}{\underset{|}{CH}}-CH_2-CH_2OH;$ (c) $\underset{O\quad O}{\overset{H_3C\quad CH_3}{\times}}$ ; or (d) $-CH\underset{OH}{\overset{O}{\diagup}}\overset{O}{\diagdown}$ ;

and the pharmaceutically acceptable salts thereof.

The present invention also includes pharmaceutical compositions containing an effective lipoxygenase inhibiting amount of compounds of the formula $$\underset{R_2}{\overset{R_1}{\text{HO}-\text{C}_6\text{H}_2-\text{SCH}_2\text{CH}_2\text{R}_3}}$$

wherein $R_1$ and $R_2$ are the same or different numbers of the group consisting of tert-alkyl of 4 to 10 carbon atoms; and $R_3$ is (a) $-\overset{OH}{\underset{|}{CH}}-CH_2-COOR_4,$ wherein $R_4$ is hydrogen or lower alkyl;

(b) $-\overset{OH}{\underset{|}{CH}}-CH_2-CH_2OH;$ (c) $\underset{O\quad O}{\overset{R_6\quad R_7}{\times}}$ wherein $R_6$ and $R_7$ may be the same or different and are alkyl of 1 to 4 carbon atoms; or (d) 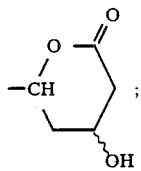

-continued
(d) 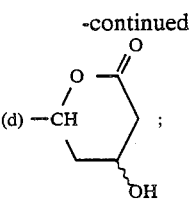

and the pharmaceutically acceptable salts thereof.

Preferred pharmaceutical compositions of the present invention are those containing an effective lipoxygenase inhibiting amount of compounds of the formula

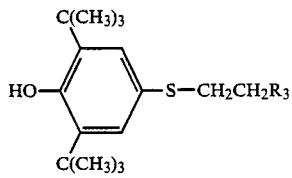

wherein $R_3$ is (a) 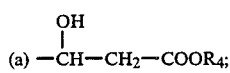

wherein $R_4$ is hydrogen or methyl;

(b) 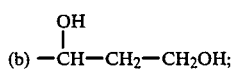

(c) 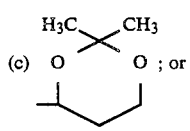 ; or and the pharmaceutically acceptable salts thereof.

Compounds described herein may be prepared by any available procedure. Compounds prepared as the acid addition salts may be converted to the free base by reaction with an appropriate base.

Compounds of the present invention are advantageously prepared by the methods outlined in Schemes I and II.

As shown in Scheme I an appropriate mercaptophenol (I) is reacted with an appropriate α, β-unsaturated carbonyl compound in the presence of triethylamine. (For example, as shown in Scheme I, the α, β-unsaturated carbonyl is acrolein.) The resulting aldehyde (II) is then reacted with lithium methyl acetate in tetrahydrofuran to give the ester (III). In the procedure IA, the ester (III) is reduced with lithium aluminum hydride to give the alcohol (IV) which is then dissolved in acetone and reacted with 2,2-dimethoxypropane in the presence of p-toluenesulfonic acid monahydrate to give compound (V).

In procedure IB, the ester (III) is reacted with trialkyl silylchloride to give the silylester (VI) which is then (1) reduced with lithium aluminum hydride, (2) oxidized to the aldehyde (VII) which is then reacted with lithium methyl acetate to give the ester (VIII). Reaction with fluoride ion gives the lactone (IX).

Scheme II shows an alternate process for preparing the lactone (IX) in which the aldehyde (II) is reacted with methylacetoacetate to give the methyl keto ester (X) which is then reduced to give the diastereomeric diols (XI A) and (XI B). Reaction with acid gives the lactone (IX).

SCHEME I

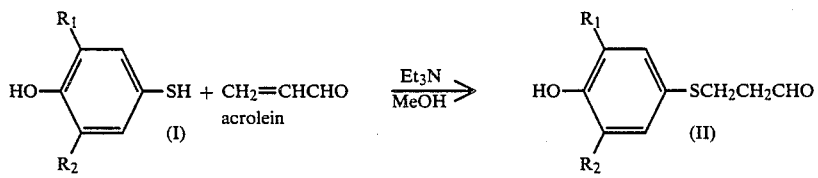

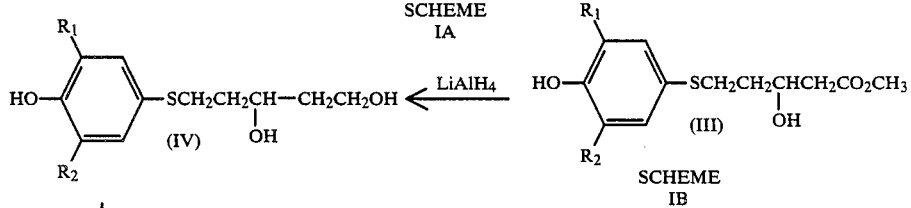

SCHEME IA

SCHEME IB

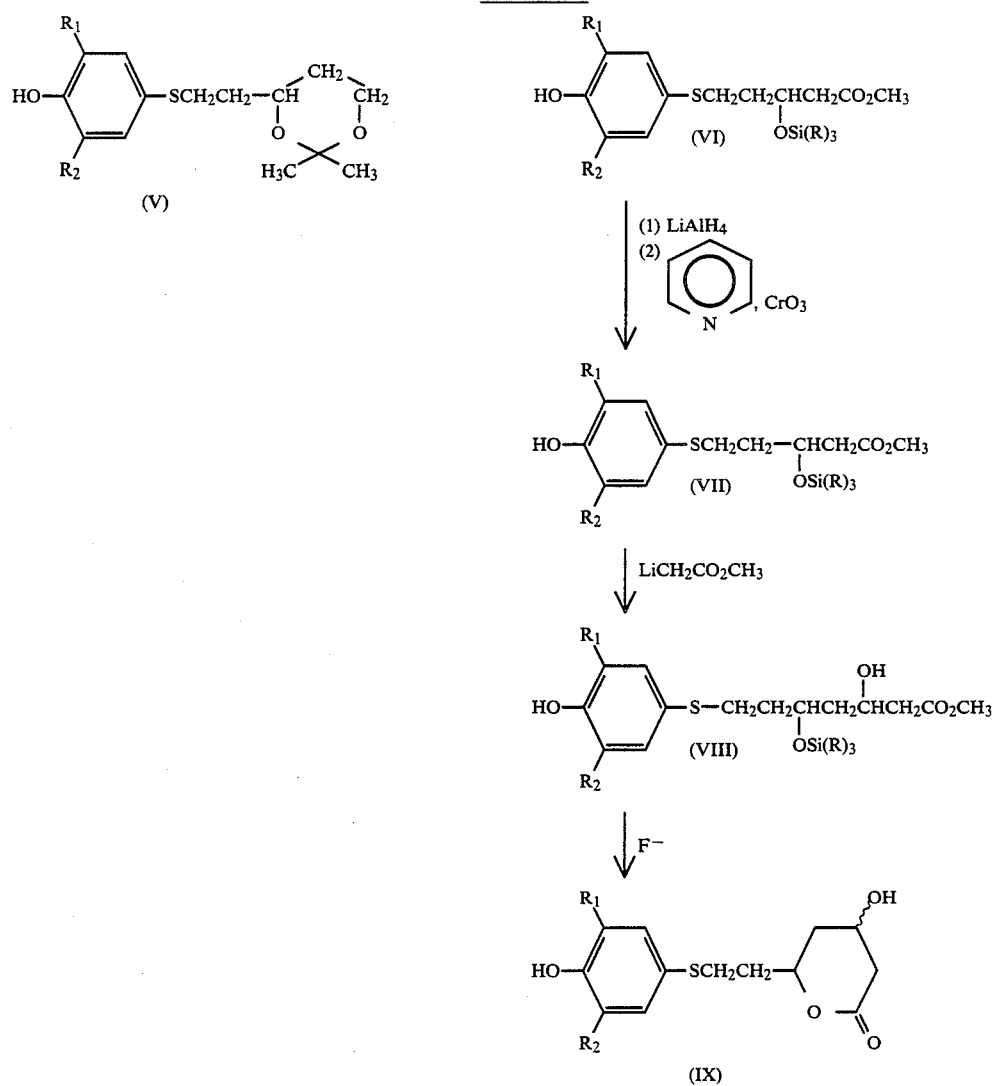
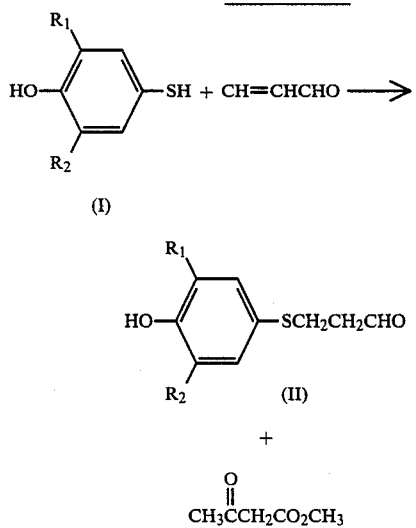
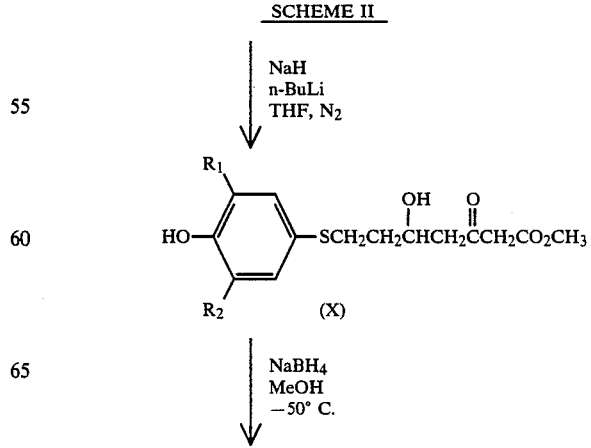

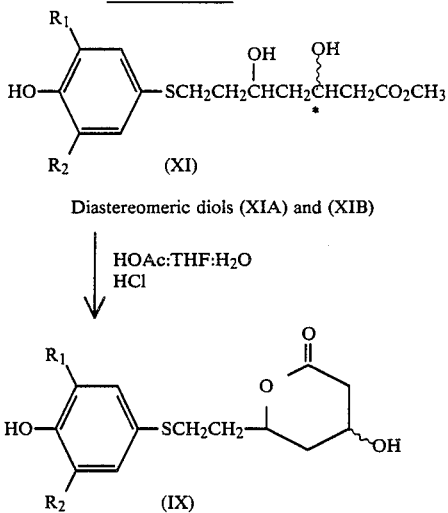

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "lower alkylene", as used herein, refers to straight or branched chain alkyl groups having from 1 to 6 carbon atoms, i.e., methylene, ethylene, n-propylene, iso-propylene, n-butylene, sec-butylene, 1,1-dimethylethylene, n-pentylene, 2-methylbutylene, 2,2-dimethylpropylene, n-hexylene, and the like.

The term "tert-alkyl" as used herein in reference to $R_1$ and $R_2$ refers to branched chain alkyl moieties of from about 4 to 10 carbon atoms having a tertiary carbon attached to the phenyl ring substituted by $R_1$ and $R_2$. Exemplary of such groups are tertiary-butyl i.e., 1,1-dimethylethyl, 1,1-dimethyl propyl, 1-methyl-1-(ethyl)pentyl, 1,1-diethylpropyl,1-ethyl-1-(propylbutyl and the like.

The expression "pharmaceutically acceptable salts" is intended to include those salts capable of being formed with the compounds of the present invention, without materially altering the chemical structure or pharmacological properties thereof. Such salts include inorganic and organic cations or acid addition salts such as sodium, potassium, calcium, ammonium, alkylammonium, etc. well known to those skilled in the art.

It will be appreciated by those skilled in the art that when $R_3$ is:

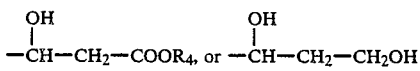

or when $R_4$ is lower alkyl an asymmetric center may exist and d and l enantiomers or diastereoisomers and mixtures may be obtained. The present invention includes such mixtures as well as the separate isomers and additionally includes the stereoisomers which occur when $R_3$ is tetrahydro-4-hydroxy-2-pyranone.

The compounds of the present invention can be administered in such oral dosage forms as tablets, capsules, pills, powders, granules, elixirs, or syrups as well as aerosols for inhalation. Likewise, administration may be effected topically, intravascularly, subcutaneously, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient; the severity of the condition to be ameliorated; and the route of administration. A physician of ordinary skill can readily determine and prescribe the effective amount of the drug required to prevent, treat or arrest the progress of the condition. Dosages of the compounds of the present invention, will range generally between about 0.1 mg/kg/day to about 100 mg/kg/day and preferably between about 0.5 mg/kg/day to about 50 mg/kg/day when administered to patients suffering from allergic or hypersensitivity reactions or inflammation. The compounds may also be administered topically to treat proliferative skin conditions such as psoriasis. The daily dosage may be administered in a single dose or in equal divided doses three or four times daily. The compounds may be administered as the sole therapeutic agent, or in combination with other agents such as cyclooxygenase inhibitors, particularly in patients who exhibit pro-inflammatory or allergic response to, for example, conventional non-steroidal anti-inflammatory agents. Parenteral, e.g., intravenous, administration is preferable if a rapid response is desired, as, for example, in some cases of asthma.

In the pharmaceutical compositions and methods of the present invention, at least one of the active compounds of the invention or a pharmaceutically acceptable salt thereof will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethycellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

The compounds of the invention are easily prepared from readily available starting materials in a conventional manner.

The selective activity of the compounds of this invention was determined using the following assay.

Determination of anti-inflammatory, anti-allergy activity: in vitro inhibition of 5-lipoxygenase The 10,000×g supernatant fraction of Rat Basophilic Leukemia Cell Homogenate (RBL-1) serves as a 5- lipoxygenase enzyme source. The enzyme is incubated with [1-$^{14}$C]-arachidonic acid and Cec$^{++}$ in the presence and absence of test compound. The product of 5-lipoxygenase, 5-hydroxyeicosatetraenoic acid (5-HETE), is separated by thin-layer chromatography and measured by radio-activity. A compound inhibiting 5-HETE synthesis by 30% or more is considered active at that concentration. Initial screening doses are $1 \times 10^{-4}$M. When the compound inhibits more than 50% of 5-HETE synthesis at $10^{-4}$M, that compound is tested at multiple dose levels to determine the IC$_{50}$ value (inhibitory concentration to inhibit 50%).

The following non-limiting examples further illustrate details for the preparation of the compounds of the present invention. Those skilled in the art will readily understand and appreciate that known variations of the conditions and procedures in the following preparative methods can be utilized. All temperatures are degrees Celcius unless otherwise noted.

EXAMPLE 1

Preparation of 3,5-bis(1,1-dimethylethyl)-4-hydroxyphenylthiocyanate

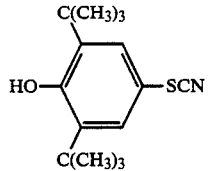

To a three-necked, round bottom 5L flask, equipped with a mechanical stirrer, gas inlet, thermometer and gas outlet, was added 2,6-di-tert-butyl- phenol (474 g, 2.30 mole), ammonium thiocyanate (76.12 g, 4.83 mole) and methanol (1200ml). The reaction mixture was stirred and cooled to 0° C. in an ice/salt bath. Maintaining the temperature at 0° C to 10° C., chlorine gas was slowly bubbled through the mixture for about 1 hour whereupon the reaction mixture was a heterogeneous yellow color. Ammonia was then bubbled through the reaction for about 1½ hours, maintaining the reaction mixture at a temperature of between 0° to 10° C. The reaction was stirred for an additional hour at 0° C., poured into 2L of cold distilled water and refrigerated overnight. The aqueous phase was decanted and the solid taken up in methanol, precipitated from water, filtered and dried for 2 days over phosphorous pentoxide. The resulting gummy yellow solid was recrystallized from pentane and dried in vacuo to yield the product as a white powder, m.p. 61.5°-63° C. Analysis calc. for C$_{15}$H$_{21}$NSO: Calc: C, 68.40; H, 8.03; N, 5.32; S, 12.17. Found: C, 68.85; H, 8.05; N, 5.29; S, 12.12.

EXAMPLE 2

Preparation of 2,6-bis(1,1-dimethylethyl)-4-mercaptophenol.

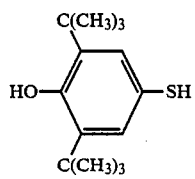

3,5-bis(1,1-dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

Preparation of 3-[[3,5-bis(1,1-dimethylethyl)-4-hydroxyphenyl]thio]-propanal.

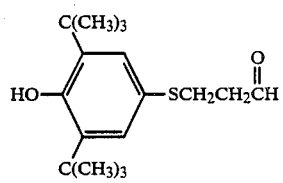

A mixture of 5.0 g of 2,6-bis(1,1-dimethylethyl)-4-mercaptophenol, 4.0 ml of acrolein, 0.5 ml of triethylamine, and 60 ml of methanol was stirred at room temperature for 17 hr. Then the mixture was distilled to dryness under reduced pressure. The residual oil was chromatographed on silica gel. The column was eluted with hexane-ethyl acetate to furnish 3-[[3,5-bis(1,1-dimethylethyl)-4-hydroxyphenyl]thio]propanal as viscous oil.

EXAMPLE 4

Preparation of methyl 5-[[3,5-bis(1,1-dimethylethyl)-4-hydroxyphenyl]thio]-3-hydroxypentanoate.

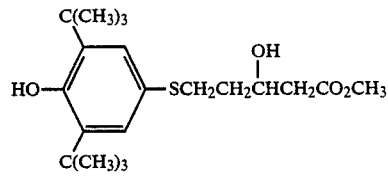

To a solution of 1.5 g of diisopropylamine in 25 ml of tetrahydrofuran (THF), stirred at −78° C. in an atmosphere of nitrogen, was added 6.5 ml of 1.6M n-butyllithium in hexane. The mixture was stirred at −78° C. for 5 min after which a solution of 1.2 g of methyl acetate in 5 ml of THF was added. The mixture was again stirred at −78° C. for 5 min. Then a solution of 1.75 g of 3-[[3,5-bis(1,1-dimethylethyl)-4-hydroxyphenyl]thio]propanal, the product of Example 3, in 20 ml of THF was added. The reaction mixture was stirred at −78° C. for ½ hr. A saturated solution of ammonium chloride was carefully added, and the resultant mixture was allowed to warm to room temperature. The mixture was extracted with ether. The ether extract was washed with water, dried over anydrous MgSO$_4$, and distilled to dryness under reduced pressure. The residual oil was chromatographed on silica gel. Elution with hexane-ethyl acetate followed by crystallization from aqueous methanol gave the product mp. 77°-80° C.

Analysis calc. for C$_{20}$H$_{32}$SO$_4$: Calc.: C,65.18; H,8.75; S,8.70, Found: C,65.32; H,8.80; S,8.80.

EXAMPLE 5

Preparation of 2,6-bis(1,1-dimethylethyl)-4-[3,5-dihydroxypentyl]thio]phenol.

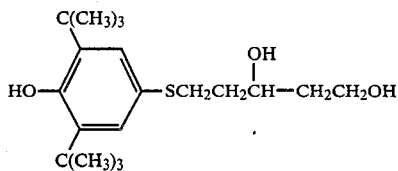

To a mixture of 500 mg of lithium aluminum hydride in 70 ml of anhydrous ether, stirred and heated under reflux, was added a solution of 1.0 g of methyl 5-[[3,5-bis(1,1-dimethyl ethyl)-4-hydroxyphenyl]thio]-3-hydroxypentanoate in 30 ml of anhydrous ether. The reaction mixture was stirred and heated under reflux for 1 hr. The reaction mixture was stirred at room temperature for an additional ¾ hr and then cooled in an ice bath. The reaction mixture was carefully treated with water, and the resultant mixture was acidified with 6N HCL. The ether phase was separated, washed with water, dried over anhydrous MgSO4, and evaporated to dryness to afford a viscous oil which solidified on standing, to give crude product mp 95°–96° C. Crystallization of the product from ether-hexane raised the mp to 107°–109° C.

EXAMPLE 6

Preparation of 4-[[2-(2,2-dimethyl-1,3-dioxan-4-yl)ethyl]thio]-2,6-bis(1,1-dimethylethyl)phenol.

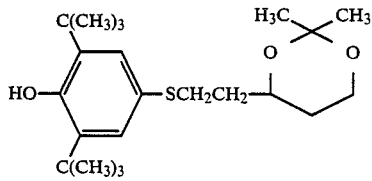

An 800 mg sample of the product of Example 5 was dissolved in 45 ml of acetone. To this solution were added ml of 2,2-dimethoxypropane and 15 mg of p-toluenesulfonic acid monohydrate. The reaction mixture was stirred and heated under reflux for 2 ¾ hr. and then allowed to stand at room temperature for ½ hr. The reaction mixture was evaporated nearly to dryness in a stream of nitrogen. The residue was diluted with ether and a 5% solution of NaHCO3. The ether phase was separated, washed with water, dried over anhydrous MgSO4, and evaporated to dryness to afford 4-[[2-(2,2-dimethyl-1,3-dioxan-4-yl)ethyl]thio]2,6-bis(1,1-dimethylethyl)phenol as a viscous oil; NMR(CDCl3):δ7.2(s, aromatic H's), 2.9(t,J=7 Hz,—SCH2—); 1.43(s,(CH3)3C—), 1.36

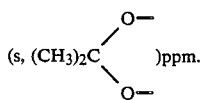

(s, (CH3)2C )ppm.

EXAMPLE 7

Preparation of methyl 7-[[3,5-bis(dimethylethyl)-4-hydroxyphenyl]thio]-5-hydroxy-3-oxoheptanoate.

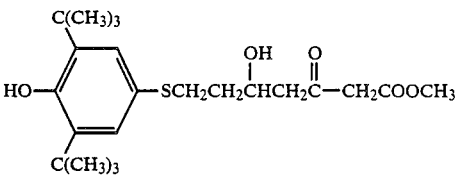

A 6.0 g sample of a 50% sodium hydride dispersion was washed free of mineral oil with hexane. After 200 ml of freshly distilled THF was added, the mixture was stirred in an ice bath in an atmosphere of nitrogen. A solution of 14.5 g of methyl acetoacetate in 50 ml of THF was added, and stirring in the ice bath was continued for 10 min. To the mixture was added 54 ml of 2.3M n-butyl lithium (in hexane). The mixture was stirred for an additional five minutes in the ice bath and then cooled to −50° C. A solution of 13.5 g of 3-[[3,5-bis(1,1)-dimethylethyl)-4-hydroxyphenyl]thio]propanal, the product of Example 3, in 150 ml of THF was added at −50° C. over a period of 10 min. The reaction mixture was stirred at −50° C. for 20 min following the addition. Then 100 ml of saturated ammonium chloride was added, and the resultant mixture was allowed to warm to room temperature. The mixture was diluted with water and then extracted with ether. The ether extract was washed with water, dried (MgSO4) and distilled to dryness under reduced pressure. The residual oil was chromatographed on silica gel to afford the title compound as an oil.

EXAMPLE 8

Preparation of methyl 7-[[3,5-bis(dimethylethyl)-4-hydroxyphenyl]thio]-3,5-dihydroxyheptanoate.

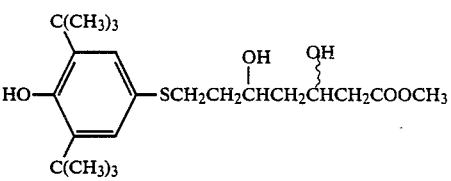

To a solution of 1.2 g of the compound of Example 7 in 65 ml of methanol, stirred at −50° C., was added 950 mg of sodium borohydride. The reaction mixture was stirred at −50° C. for 15 min and then allowed to warm to room temperature. The reaction mixture was acidified with 2% HCl. The acidified mixture was extracted with ether. The ether extract was washed with water, dried (MgSO4), and distilled to dryness under reduced pressure. The residual oil was chromatographed on silica gel to afford the product as a pair of diastereomeric diols, A and B.

EXAMPLE 9

Preparation of (A)(±)6-[2-[[3,5-bis(1,1-dimethylethyl)-4-hydroxyphenyl]thio]ethyl]]tetrahydro-4R-hydroxy-2-pyranone and (B)(±)6-[2-[[3,5-bis(1,1-dimethylethyl)-4-hydroxyphenyl]thio]ethyl]]tetrahydro-4S-hydroxy-2-pyranone.

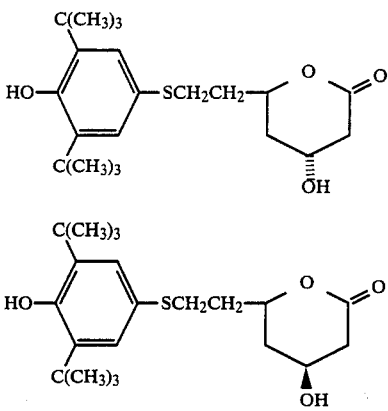

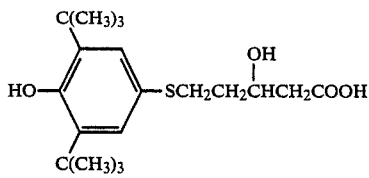

A mixture of 1.8 g of the diol (A) of Example 8, 20 ml of a 20:10:2 mixture of HOAc:THF:H₂O, and 0.1 ml of 12N HCl was stirred at room temperature for 17 hr after which it was diluted with water. The resultant mixture was extracted with ether. The ether extract was washed successively with water, 5% NaHCO₃, and water again, dried (MgSO₄), and distilled to dryness under reduced pressure to afford an oil. The oil was chromatographed on silica gel to furnish the diastereoisomer (A)(±)6-[2-[[3,5-bis(1,1-dimethylethyl)-4-hydroxyphenyl]thio]ethyl]tetrahydro-4R-hydroxy-2-pyranone which was crystallized from ether-hexane.

Analysis calcd for $C_{21}H_{32}SO_4$: Calc.: C,66.28; H,8.48 Found: C,66.22; H,8.73

In like manner, the diol (B) of Example 8 was converted to the diasteromer (B) which is (±)6-[2-[[3,5-bis(1,1-dimethyl-ethyl)-4- hydroxyphenyl]thio]ethyl]-tetrahydro-4S-hydroxy-2-pyranone.

EXAMPLE 10

Methyl 5-[[3,5-bis(1,1-dimethylethyl)-4-hydroxyphenyl]thio]-3-hydroxypentanoic acid.

0.5 G of the product of Example 4 was added to a solution of 50 mg of lithium hydroxide in 15 mL of methanol under argon gas and the solution was stirred for 5 hr at room temperature. The reaction solution was added with stirring to about 100 mL of 4% hydrochloric acid at ice-bath temperature, and the title compound was crystallized. Recrystallization from hexane gave product mp(dsc) about 87° C., ir (KBr) 3400-2800 (OH), 1700 (C=O) cm⁻1.

While the invention has been described and illustrated with reference to certain preferred embodiments thereof, those skilled in the art will appreciate that various changes, modifications, and substitutions can be made therein without departing from the spirit of the invention. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A method for treating lipoxygenase mediated conditions in mammals comprising administering to a mammal in need of such treatment a therapeutically effective amount of a compound of the formula:

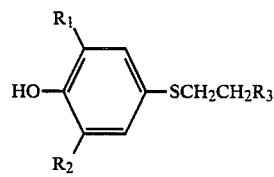

where $R_1$ and $R_2$ are the same or different members of the group consisting of tert-alkyl of 4 to 10 carbon atoms; and $R_3$ is

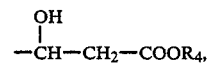

wherein $R_4$ is hydrogen or lower alkyl; or a pharmaceutically acceptable salt thereof, together with one or more non-toxic pharmaceutically acceptable carriers.

2. A method according to claim 1 wherein said compound is of the formula:

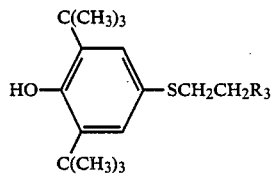

wherein $R_3$ is

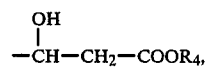

wherein $R_4$ is hydrogen or methyl.

3. A method according to claim 2 wherein said compound is methyl 5-[[3,5-bis(1,1-dimethylethyl)-4-hydroxyphenyl]thio]-3-hydroxy pentanoate.

4. A method according to claim 2 wherein said compound is methyl 5-[[3,5-bis(1,1-dimethylethyl)-4-hydroxyphenyl]thio]-3-hydroxypentanoic acid.

5. A pharmaceutical composition for use in the treatment of lipoxygenase mediated conditions in mammals comprising a pharmaceutically effective amount of at least one compound of the formula:

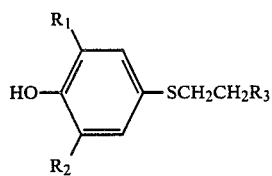

wherein $R_1$ and $R_2$ are the same or different members of the group consisting of tert-alkyl of 4 to 10 carbon atoms; and $R_3$ is

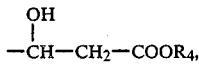

wherein $R_4$ is hydrogen or lower alkyl; or a pharmaceutically acceptable salt thereof, together with one or more non-toxic pharmaceutically acceptable carriers.

6. A pharmaceutical composition according to claim 5 wherein said compound is of the formula:

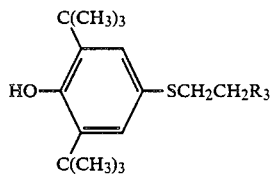

wherein $R_3$ is

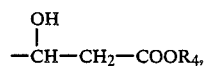

wherein $R_4$ is hydrogen or methyl.

7. A pharmaceutical composition according to claim 6 wherein said compound is methyl 5-[[3,5-bis(1,1-dimethylethyl)-4-hydroxyphenyl]-thio]-3-hydroxy pentanoate.

8. A pharmaceutical composition according to claim 6 wherein said compound is methyl 5-[[3,5-bis(1,1-dimethylethyl]-4-hydroxyphenyl)-thio]-3-hydroxypentanoic acid.

* * * * *

UNITED STATES PATENT AND TRADEMARK OFFICE
CERTIFICATE OF CORRECTION

PATENT NO. : 4,801,611
DATED : Jan. 31, 1989
INVENTOR(S) : Chinn, et al.

It is certified that error appears in the above-identified patent and that said Letters Patent is hereby corrected as shown below:

Column 10, the continuation of Scheme I, the third structure, that portion of the structure reading "-$CHCH_2CO_2CH_3$" should read -- -$CHCH_2CHO$ --.

Column 12, line 67, reading "10,000Xg" should read -- 100,000Xg --.

Column 15, line 45, reading "ml" should read -- 9 ml --.

Column 15, line 53, reading "MgS04" should read -- $MgSO_4$ --.

Column 17, line 50, reading "50 mg" should read -- 350 mg --.

Signed and Sealed this

Fourteenth Day of May, 1991

Attest:

Attesting Officer

HARRY F. MANBECK, JR.

Commissioner of Patents and Trademarks